US00RE40796E

(19) United States
(12) Reissued Patent
O'Neill

(10) Patent Number: US RE40,796 E
(45) Date of Reissued Patent: Jun. 23, 2009

(54) BONE HARVESTING METHOD AND APPARATUS

(75) Inventor: Michael J. O'Neill, Scituate, MA (US)

(73) Assignee: Paradigm BioDevices, Inc., Rockland, MA (US)

(21) Appl. No.: 09/922,555

(22) Filed: Aug. 3, 2001

Related U.S. Patent Documents

Reissue of:
(64) Patent No.: 5,954,671
Issued: Sep. 21, 1999
Appl. No.: 09/221,240
Filed: Dec. 28, 1998

U.S. Applications:
(60) Provisional application No. 60/082,340, filed on Apr. 20, 1998.

(51) Int. Cl.
*A61B 10/00* (2006.01)
*A61B 17/14* (2006.01)

(52) U.S. Cl. ..... 600/567; 806/179
(58) Field of Classification Search ..... 600/566, 600/567; 606/172, 179, 170, 180, 96, 80, 606/159, 102; D15/138; 408/204, 207, 203.5; 30/113.1, 174
See application file for complete search history.

(56) References Cited

U.S. PATENT DOCUMENTS

| | | | | | |
|---|---|---|---|---|---|
| 1,493,240 | A | * | 5/1924 | Bohn | 606/170 |
| 3,990,453 | A | * | 11/1976 | Douvas et al. | 30/174 |
| 4,461,305 | A | * | 7/1984 | Cibley | 600/567 |
| 4,512,344 | A | * | 4/1985 | Barber | 606/170 |
| 4,782,833 | A | | 11/1988 | Einhorn et al. | 128/310 |
| 4,895,166 | A | * | 1/1990 | Farr et al. | 606/159 |
| 5,012,818 | A | * | 5/1991 | Joishy | 600/567 |
| 5,019,088 | A | * | 5/1991 | Farr | 606/159 |
| 5,324,300 | A | | 6/1994 | Elias et al. | 606/180 |
| 5,341,816 | A | * | 8/1994 | Allen | 600/567 |
| 5,488,958 | A | | 2/1996 | Topel et al. | 128/754 |
| 5,492,130 | A | * | 2/1996 | Chiou | 600/567 |
| 5,556,399 | A | | 9/1996 | Huebner | 606/80 |
| 5,577,517 | A | | 11/1996 | Bonutti | 128/898 |
| 5,655,542 | A | * | 8/1997 | Weilandt | 600/567 |
| 5,687,739 | A | * | 11/1997 | McPherson et al. | 600/567 |
| 5,807,276 | A | | 9/1998 | Russin | 600/567 |
| 5,833,628 | A | | 11/1998 | Yuan et al. | 600/567 |
| 5,919,196 | A | * | 7/1999 | Bobic et al. | 606/96 |
| 6,071,284 | A | * | 6/2000 | Fox | 606/102 |
| 6,139,509 | A | | 10/2000 | Yuan et al. | 600/567 |

OTHER PUBLICATIONS

BioMedical Enterprises. Inc.: "Bone and Marrow Collection System" Promotional Literature.*
"Acumed™ Bone Graft System", Promotional Literature.
Bio Medical Enterprises, Inc., "The BoneHOG™; Bone and Morrow Collection System," Promotional Literature.
SpineTech, Inc., "Bone Harvester Kit," Promotional Literature.
Kreibich et al., "Donor Site Morbidity at the Iliac Crest: Comparison of Percutaneous and Open Methods," *J. Bone Joint Surg.*(Br) 1994: 76–B: 847–8.
Nish, Iain, "Trephined Cancellous Cores Improve Iliac Crest Donor Site Morbidity in 54 Patients," Abstract.
McGurk et al., "The Trephining of Bone from the Iliac Crest: an Anterior Approach," *Int. J. Oral Maxillofac. Surg.*1993; 22:87–90.

* cited by examiner

*Primary Examiner*—Julian W Woo
(74) *Attorney, Agent, or Firm*—Bromberg & Sunstein LLP

(57) ABSTRACT

An apparatus and method for harvesting bone using a manual, cylindrical, multi-directional coring device with a guided delivery system that can be inserted through a percutaneous or closed approach to extract precisely measured amounts of bone or bone marrow. A series of guide wires, obturators, dilators and cannulas are used as the exposure and delivery instrumentation for a cutting tool. The cutting tool has a tip with six cutting edges for cutting in all directions.

18 Claims, 6 Drawing Sheets

BONE HARVESTING METHOD AND APPARATUS

Matter enclosed in heavy brackets [ ] appears in the original patent but forms no part of this reissue specification; matter printed in italics indicates the additions made by reissue.

This application claims benefit of provisional application Ser. No. 60/082,340 filed Apr. 20, 1998.

BACKGROUND OF THE INVENTION

A percutaneous, closed, or mini-open bone harvesting method for orthopedic, neurosurgical, ear nose & throat (ENT), oral, maxillo-facial, rheumatology, and bone marrow aspiration procedures.

Orthopedic, neurosurgical, spinal, ear-nose-throat, oral-maxillo-facial, and rheumatology procedures require the removal of bone or bone cells to culture or place in other parts of the body to permit fusion or bone formation. The current method for bone harvesting requires an open surgical procedure involving wide exposure of the iliac crests, ulna, radius, or femur. These areas are exposed with an incision over the donor sites, followed by the stripping of muscle to expose the donor site area. The removal of the bone is performed utilizing curettes, drills, or free-hand bone coring devices.

These open procedures usually cause very frequent donor site pain and morbidity as they involve significant incisional scarring, vast muscle stripping, damage to surrounding tissues, and over harvesting of the donor site. This has become one of the greatest complaints and problems of patients recovering from surgeries involving bone and bone marrow harvesting procedures.

Recently, inventors have begun creating "minimally invasive" methods to harvest bone. U.S. Pat. No. 5,556,399 to Huebner (1995) discloses a "coring drill used to harvest bone from a donor area of the human body." This stainless steel device is the first device of its nature, and it is used freehand, under power, without guided controls and requires an open incision with wide muscle re-section.

In 1997, Spinetech, Inc. (Minneapolis, Minn.) released a patent pending "minimally invasive" cylindrical bone harvester that is used through a mini-open procedure, but without guided control. This device is not applicable to a percutaneous technique because it requires a large incision and muscle stripping to expose the donor site. The cutter is inserted into the donor site bone freehand. More importantly, the cutter tip is a uni-directional threaded two piece unit which must be disassembled to remove bone tissue from the collection tube. This makes the device unsuitable to a closed or percutaneous procedure due to the potential for disassembly inside the patient. Bi-directional cutting action will dislodge the cutter tip from the shaft.

Biomedical Enterprises, Inc. (San Antonio, Tex.) created the patent pending Bone & Marrow Collection System (BMCS), which utilizes a manual or motor driven drill bit and a disposable collection tube. This technique provides limited initial drill stabilization, but does not guide or control the direction of the tip after cutting action begins. In addition, it still utilizes an open procedure and vast muscle resection. The BMCS is an auger-drill type that is lacking an adequate delivery system for placing the guidance tube through a percutaneous or closed technique. Also, the BMCS does not prevent the drill cutter from advancing too far into the donor site, thus violating the surrounding bony architecture, tissue, and muscle. The BMCS also does not provide an accurate and easy method to measure the amount of material captured by the drill and collection tube, and is extremely susceptible to frequent clogging during repositioning of the tip.

SUMMARY OF THE INVENTION

This invention relates to a disposable or reusable bone harvester specifically designed to operate through percutaneous, closed, or mini-open incisions during orthopedic, neurosurgical, ENT, oral-maxillofacial, rheumatology, and bone marrow aspiration procedures.

The present invention discloses a manual, cylindrical, multi-directional coring device utilizing a guided delivery system that can be inserted through a percutaneous or closed approach to extract precisely measured amounts of bone or bone marrow. The invention requires only a small incision, less that 2 cm above the donor site, and utilizes a guided delivery system of guide wires, obturators, dilators, and cannulas. The present invention makes a very small incision that gradually splits the muscle and tissue. The result is less blood loss, less tissue damage, and less donor site morbidity.

All other techniques including Huebner's, Spinetech's, and BME's require an open or mini-open incision. The first two techniques do not possess a method for guided control of the cutter tip, and the last gives only limited direction prior to the coring procedure. The disadvantages of the above techniques are:

(A) A large or mini-open incision is required resulting in incisional scarring, greater blood loss, and exposure to airborne contaminants.

(B) Huebner, Spinetech, and BME all have uni-directional cutting tips.

(C) Spinetech's cutter has two pieces and can disassemble if used in a rocking motion. BME's collection tube can not fit through cannulas to guide the approach. These devices are not applicable to a closed percutaneous technique.

(D) All require a large open incision resulting in subsequent muscle stripping to expose donor site causing increased tissue damage, blood loss, and post-op pain.

(E) All require wide dissection and over harvesting of donor site due to inability to appropriately measure quantities of bone harvested resulting in greater blood loss, post-operative pain, increased recovery time, and donor site morbidity.

(F) All can potentially cause muscle and tissue destruction and/or bony fracture as a result of misguided or uncontrolled cutter tips.

(G) Coring depths are not controlled by depth stops on any of the existing inventions.

Accordingly, it is an object of the present invention to provide a method which permits bone to be harvested in precise quantities via a percutaneous or closed technique utilizing a series of guide wires, obturators, dilators, and cannulas as the exposure and delivery instrumentation for the cutting tool.

It is another object of the present invention to provide a multi-directional cutting tip with six cutting edges, which can be used to cut in clockwise, counterclockwise, or both directions, as well as with a downward force for rapid cutting action and morselization of graft material.

It is still another object of the present invention to provide multiple cannula sizes and shapes to accommodate different anatomic sites for a more precise fit, control, and tissue protection.

A further object of the present invention is to provide distal arms, or "teeth", on the cannulas for stabilization and lateral control, which permit the cannula to move in an arc on the bony surfaces, facilitating multi-directional coring or sweeping of bone through the same incision.

Another object of the present invention is to provide a precise measurement system visible and calibrated along the proximal cylinder shaft to indicate depth of insertion and amount of material collected.

It is still another object of the present invention to provide a transparent, or translucent, bio-compatible, plastic cylindrical cutter shaft with a bonded, mechanically fastened, or ultrasonically welded permanently affixed stainless steel cutting tip forming a one-piece coring unit.

It is a further object of the present invention to provide a detachable and re-attachable T-Handle and/or Teardrop Handle.

It is also an object of the present invention to provide a calibration system on the proximal end of cutter shaft and a depth stop system to prevent the cutter from over harvesting bone, and advancing too far in the body.

Further objects of the invention may be provided with multiple sized cutting tips ranging in sizes from 8 mm, 10 mm, 12 mm, and 14 mm. These cutters can be utilized via laparoscopic techniques in addition to percutaneous, closed, and mini-open approaches.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 1:
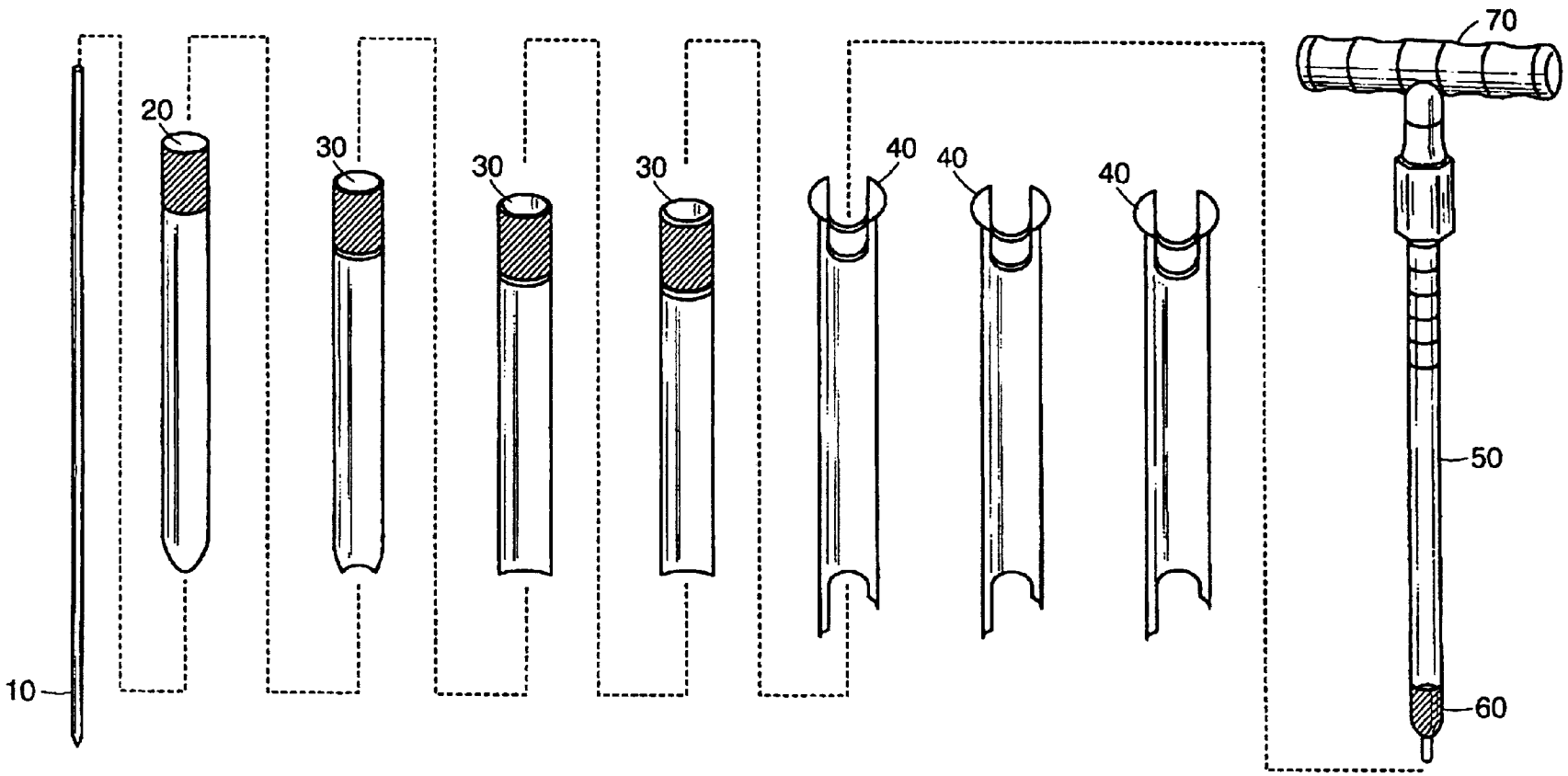
FIG. 1 is an assembly illustration of the apparatus of the present invention.

Referring to the drawings in detail wherein like elements are indicated by like numerals, there is shown a bone harvesting method and apparatus used therein. As may be most clearly seen from FIGS. 1 through 6, the apparatus is comprised of a guidance system and cylindrical coring device for extracting precise amounts of bone 1 or bone marrow 2. The apparatus system contains an elongated, generally cylindrical guide wire 10, a generally cylindrical obturator 20 with an internal, hollow channel 21 formed along its elongated central axis and positioned concentrically over the guide wire 10, a generally cylindrical, hollow dilator/toothed cannula 30 concentrically positioned over the obturator 20, and a generally cylindrical, hollow forked cannula 40 concentrically positioned over the dilator 30. The guide wire 10, obturator 20 and dilator 30 are then removed and replaced with the cutter cylinder 50 with handle 70 attached.

The guide wire 10 is elongated and preferably made from stainless steel and has nominal dimensions of 3.2 mm×25 cm. The guide wire 10 has a pointed distal end 11 and a blunt proximal end 12. The distal end 11 is defined as that end engaging a harvest site 3. The obturator 20 is also preferably made from stainless steel and has a generally cylindrical shape. The obturator 20 has a dome-shape distal end 22 and a cross-hatched proximal end 23. The proximal end 23 is cross-hatched to provide a better grip. The distal end 22 is used to split tissue for cannula placement as described below. A generally cylindrical channel 21 is centrally formed within the obturator 20 along its central, elongated axis extending from the distal end 22 to the proximal end 23. The obturator 20 is placed over the guide wire 10 by positioning the obturator 20 so that its channel 21 is slid over the wire 10. The dilator/toothed cannula 30 is also preferably made from stainless steel and has a cylindrical channel 31 is formed therein along its central, elongated axis extending from an open distal end 32 to an open proximal end 33. There may be several dilators 30 having varied lengths, outer diameters and inner diameters. Each distal end 32 is beveled with teeth at its distal tip 34 similar to a hole saw. The forked cannula 40 is hollow and has a distal end 42 and a proximal end 41. The distal end 42 is longitudinally notched resulting in two protruding arms 43 parallel to the central axis of the cannula 40. The proximal end 41 terminates in two, parallel, block-like elements 44. The forked cannula 40 is also preferably made from stainless steel and may have various inner and outer diameters and lengths. The cutter cylinder 50 has a proximal end 54 and distal end 55 with a hollow, transparent, or translucent, cylindrical biocompatible plastic tube 51 between. The distal end 55 has an attached stainless steel cutting tip 60. The cutting tip 60 may be permanently attached by bonding means of mechanically fastened or ultrasonically welded. The cutter cylinder proximal end 54 has a groove 56 for mating with a T-handle 70. The cutter cylinder 50 is nominally twenty-two centimeters in length, and comes in nominal eight, ten, twelve and fourteen centimeter diameters.

The cutting tip 60 has a proximal end 68 which attached to the cutter cylinder distal end 55. The distal end 61 of the cutter tip 60 has two, protruding, generally triangular blades 62 with four cutting edges 63 to facilitate bi-directional cutting action. The protruding blade tips 64 are connected to each other. The cutter tip distal end 61 also terminates in two cutting edges 65 positioned between the protruding cutting blades 62 for multi-directional and downward cutting action. See, especially, FIGS. 6A and 6B. As stated above the cutter cylinder proximal end 54 is joined to a T-handle 70 by means of an interference lock 72 on the T-handle distal end 71. The interference lock 72 is comprised of a threaded and/or spring loaded section that interfaces and locks the cutter cylinder proximal end 54 to the handle 70. The invention apparatus also includes an offset plunger 80 with a circular foot 81 on its distal end 82, said foot 81 being adapted to push harvested bone 1 or bone marrow 2 out of the cutter cylinder tube 51.

Figure 3:
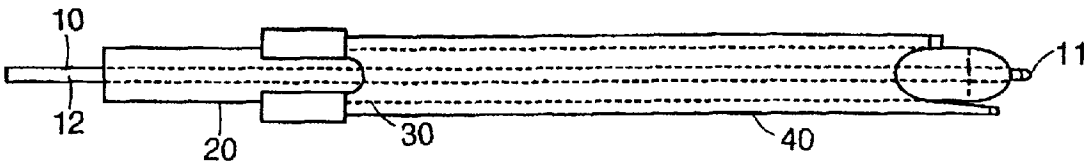
FIG. 3 is an assembled illustration of the guide wire, obturator and forked cannula.
Figure 4:
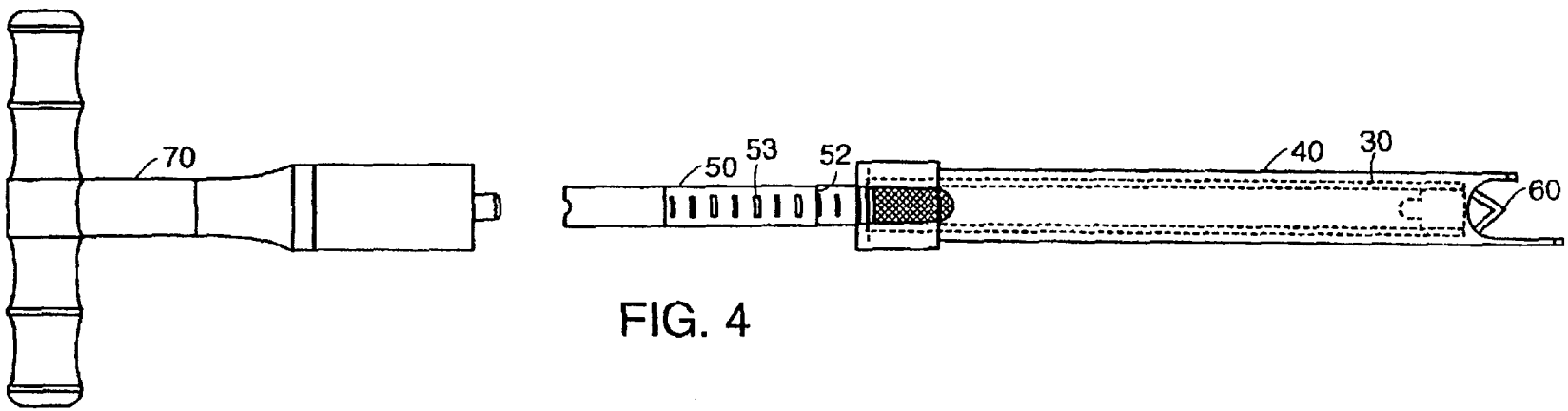
FIG. 4 is an assembly illustration of the forked cannula, dilator/toothed cannula, cutter cylinder and handle.
Figure 5:
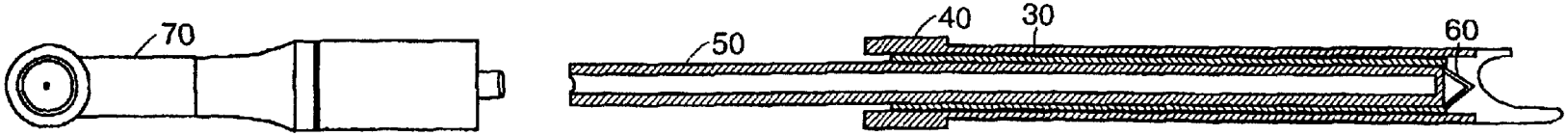
FIG. 5 is a cross-sectional view of FIG. 4.
Figure 6A:
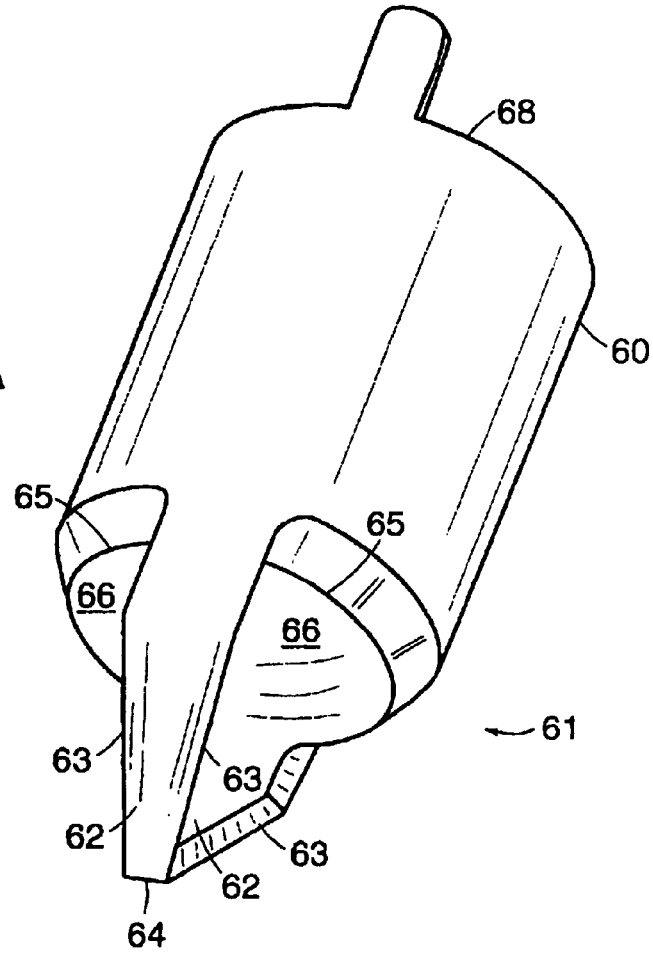
FIG. 6A is a perspective view of the cutter tip of the cutter cylinder.
Figure 6B:
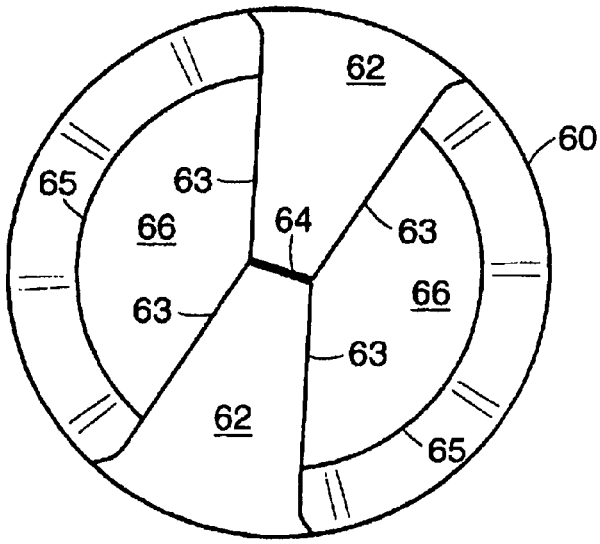
FIG. 6B is a bottom view of the cutter tip.
Figure 7A:
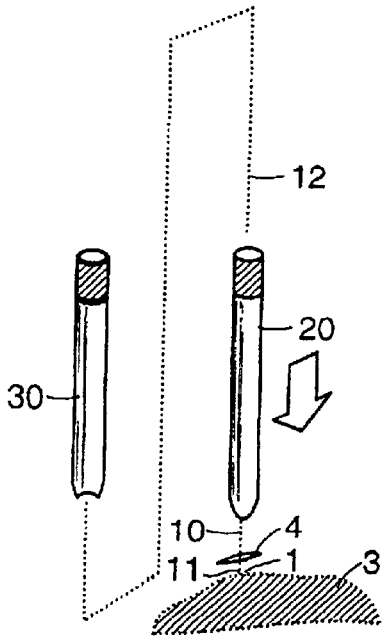
FIG. 7A is an illustration showing the first major step of the present invention method for an iliac crest harvest.
Figure 7B:
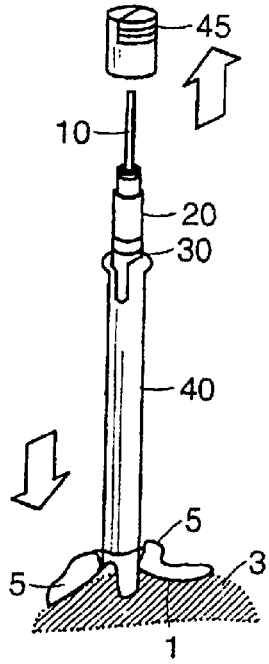
FIG. 7B shows the second major step of the method.
Figure 7C:
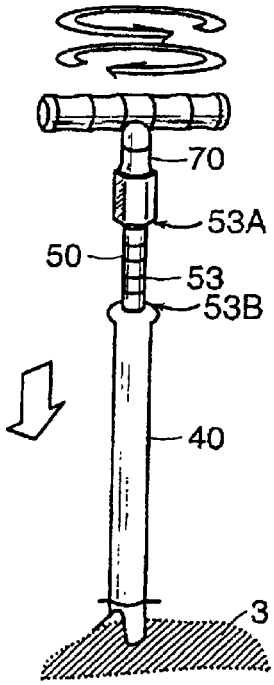
FIG. 7C shows the third major step of the method.
Figure 7D:
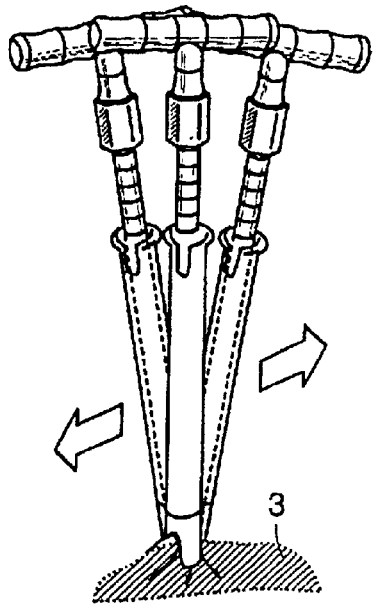
FIG. 7D shows the fourth major step of the method.
Figure 8:
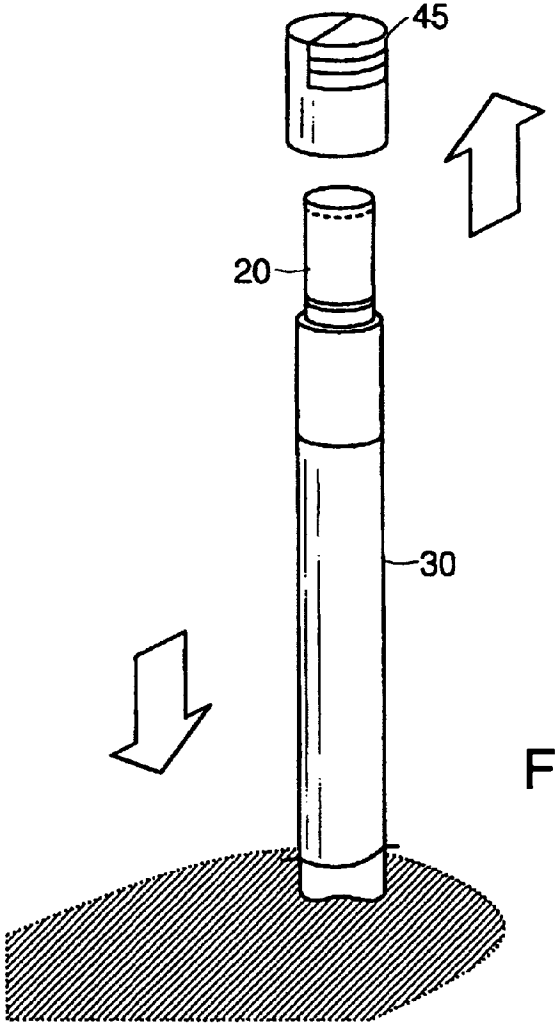
FIG. 8 is an illustration showing the first major step of the present invention for other donor sites.
Figure 7E:
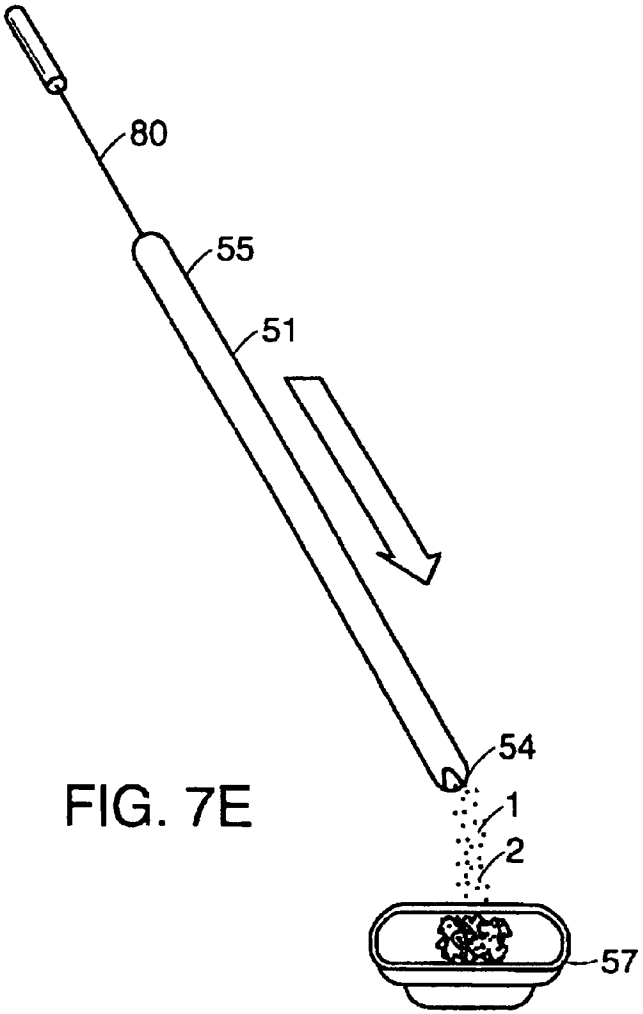
FIG. 7E shows the fifth major step of the method.

FIGS. 3, 4 and 5 illustrate the apparatus in the varying configurations required for the invention method. FIG. 3 illustrates the invention assembly in an exposure mode, which includes the wire guide 10, obturator 20, dilator 30, and forked cannula 40. FIG. 4 is an assembly illustration of the handle 70, cutter cylinder 50, dilator 30 and forked cannula 40 in a working model. FIG. 5 is a cross-section view of the assembly of FIG. 4. Referring also to FIGS. 7A through 8, the guide wire 10 is inserted through an incision 4 two centimeters or less until it abuts bone 1. The guide wire proximal end 12 is gently tapped so that the guide wire distal end 11 enters into bone 1. An obturator 20 is placed over the guide wire 10 to split muscle 5 over and around the guide wire 10 to create a wider working area until it abuts bone 1. A dilator 30 is placed over the obturator 20 and guide wire 10 and continues to split muscle 5 as it is moved forward over the donor graft site 3. A forked cannula 40 is then placed over the dilator 30, obturator 20 and guide wire 10 until it abuts bone 1. The guide wire 10 and obturator 20 are removed leaving a clear working channel through the forked cannula 40 and dilator 30. The forked cannula 40 is gently tapped into final position over the harvest site 3. The cutter cylinder 50 is attached to the handle 70 and inserted into the cannulas 30, 40. The cannulas 30, 40 protect the cutter cylinder 50 and provide guided control for the cutter cylinder 50 and its cutting tip 60. As may be most clearly seen from FIGS. 7C and 7D, the combination of handle/cutter cylinder/cutting tip 70, 50, 60 is manually rotated into bone 1 in either a clockwise, counterclockwise, downward, and/or rocking fashion with both an uni-directional, bi-directional, and/or multi-directional cutting action. Bone 1 and/or bone marrow 2 material is captured in the cutter cylinder tube 51. The handle 70 is detached from the cutter cylinder tube 51 and the captured material 1, 2 is pushed out with the offset plunger 80. See FIG. 7E.

Figures 2A, 2B, 2C, 2D, 2E, 2F, 2G:
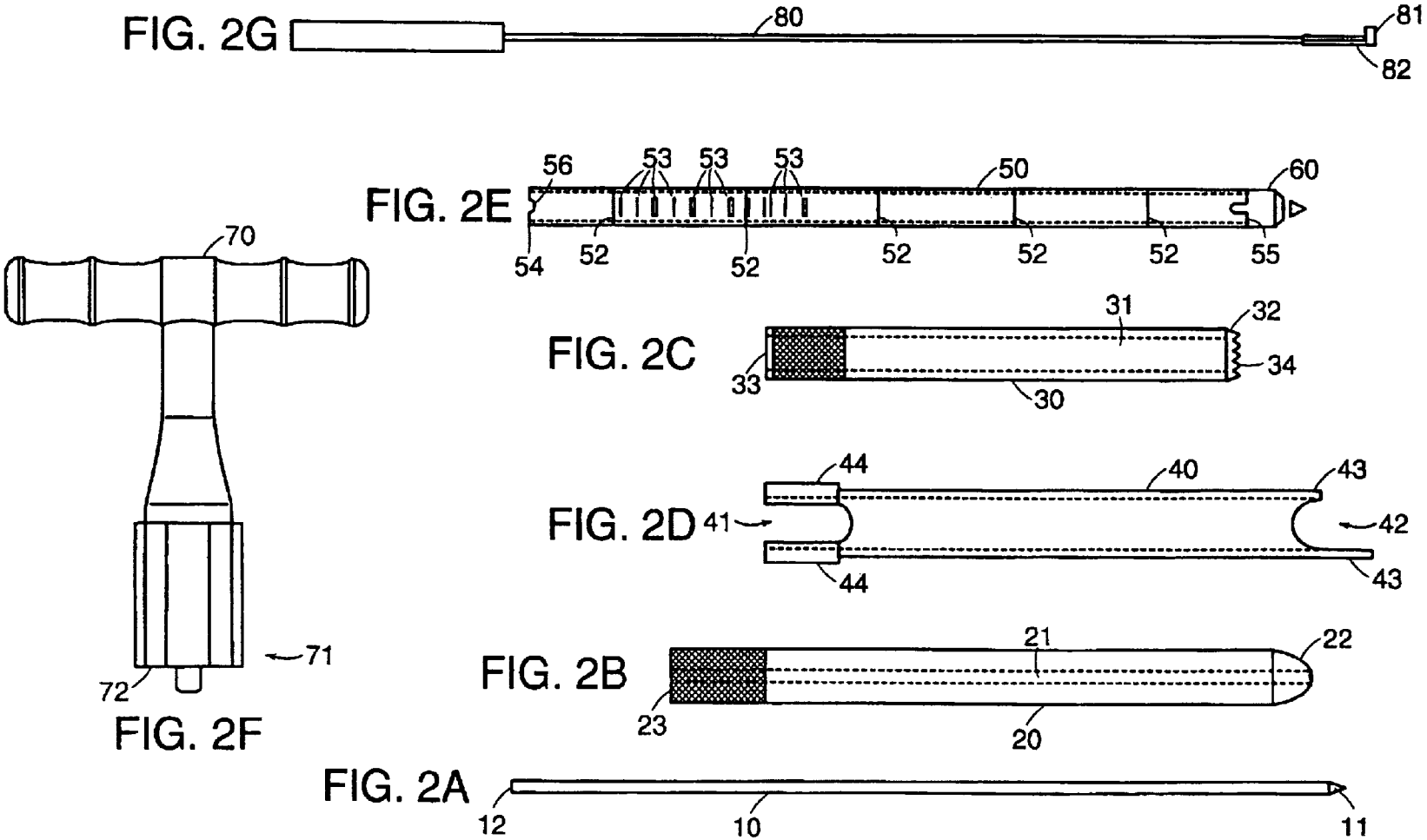
FIG. 2A is an illustration of the guide wire portion of the invention.
FIG. 2B is an illustration of the obturator portion of the invention.
FIG. 2C is an illustration of the dilator/toothed cannula portion of the invention.
FIG. 2D is an illustration of the forked cannula portion of the invention.
FIG. 2E is an illustration of the cutter cylinder portion of the invention.
FIG. 2F is an illustration of the handle portion of the invention.
FIG. 2G is an illustration of the offset plunger portion of the invention.

Referring specifically to FIGS. 2E, 4 and 5, the cutter cylinder 50 is comprised of an elongated biocompatible polycarbonate cylindrical collection shaft 51 with a permanently attached, ultrasonically welded, bonded, or mechanically fastened stainless steel cutting tip 60. The cutter cylinder 50 may have multiple sizes including outside diameters of eight mm, ten mm, twelve mm, and fourteen mm diameters. The cutter cylinder 50 has two sets of printed, laser-etched, and/or silk-screened calibrations 52, 53. The first set of calibrations 52 are cubic centimeter readings indicating the volume of material captured in the tube 51. The second set of calibrations 53 are a built in depth measurement in centimeters fully readable with insertion of the cutter cylinder 50 through the dilator 30 and forked cannula 40. As the cutter cylinder 50 is placed into the cannulas 30, 40, the calibration reading 53B will meet the proximal end 41 of the forked cannula 40 and will indicate a zero centimeter depth. As the cutter cylinder cutter tip 60 is enters into bone 1 the shaft 51 will move downward into the cannulas 30, 40. The calibration reading 53A will indicate that the cutter tip 60 has advanced five centimeters.

Referring again to FIGS. 6A and 6B, the cutting tip 60 is a preferably made from stainless steel. The cutting tip 60 is hollow thereby permitting material from the cutting action to pass back into the cutter tip distal end 61. The radial separation between cutting blades 62 is nominally 135 degrees to allow harvested material to pass into the cutting tip hollow interior 66. The cutting blades 62 are flat and each formed at a 45 degree angle to the central longitudinal axis of the cutting tip 60. The cutting edges 65 are also formed generally at a 45 degree angle to the central longitudinal axis of the cutting tip 60.

As may be most clearly seen from FIGS. 7 through 8, the method of the present invention utilizing the present invention apparatus is illustrated for an iliac crest harvest and is as follows. First, a small incision 4 of less than two centimeters is made above the harvest site 3 to expose it. The medial wall of iliac crest is identified. A guide wire 10 having a pointed distal end 11 and blunt proximal end 12 is inserted into the incision 4, distal end 11 first, and is positioned onto the medial superior surface of anterior or posterior iliac spine and is gently tapped into position into cortical bone 1. An obturator 20 with hollow channel 21 is placed over the guide wire 10 and is guided down into the incision 4, thus gradually splitting muscle 5 and tissue, until it contacts bone 1. One or more dilators 30 are placed over the obturator 20 and guide wire 10 increasing the incision 4 according to a percutaneous approach. Up to three dilators 30 may be used where necessary to split tissue for the next major step. Next, a forked cannula 40 is placed over the dilator/s 30, obturator 20, and guide wire 10 until it is on the harvest site 3. The guide wire 10 and obturator 20 are then removed to create a working channel for the cutter cylinder 50. One or more dilators 30 may also be removed. An impactor cap 45 is placed over the cannula distal end 42 and gently tapped into position over the harvest site 3. This facilitates guided control of the cutter tip 60, and shields adjacent structures from subsequent damage. Moreover, the forked cannula 40 has protruding arms 43 enabling it to straddle or grab bone 1. A cutter cylinder 50 is then joined to a handle 70. The cutter cylinder 50 is then inserted into the cannula 40, cutting tip 60 first. Bone 1 is then harvested with a slight downward pressure and uni- or bi-directional rotation. Bone material will enter through the cutting tip interior 66 into the cutter cylinder tube 51. The depth calibrations 53 on the tube 51 provide measurements to determine insertion depth. In addition to protecting tissue, and guiding the cutter tip 60, the forked cannula 40 also permits the cutting tip 60 to be maneuvered in an arcing motion to drill or sweep greater surface areas. This permits the cutting tip 60 to harvest bone 1 in multiple directions through the same incision 4 to collect greater quantities of material, without the captured material jamming or impeding the cutting tip 60. Bone is then retrieved through precise measurements via calibrations on the cutter cylinder shaft 51 which are visible as the cutting tip 60 cores bone 1. To collect greater amounts of bone, the forked cannula 40 may be rotated in multiple directions to channel more bone from the harvest site 3. To remove the harvested bone material, the cutter cylinder tube 51 is removed from the handle 70. The cutter cylinder proximal end 54 is positioned over a basin 57, implant, or fusion site. Bone material is pushed out of the cutter cylinder tube 51 with the offset plunger 80. When the appropriate amount of bone has been removed, the invention apparatus is removed from the incision 4 and the surgeon closes.

Although the iliac crest is the most popular area harvested, other anatomical sites may be indicated. For these areas, a small incision above the harvest site is made and the guide wire 10 inserted into cortical bone. An obturator 20 and dilator/toothed cannula 30 are placed over the wire guide 10. The wire guide 10 and obturator 20 are removed and an impactor cap 45 is placed over the cannula 30 and tapped gently into the cortical surface. The methodology of using the cutter cylinder 50 as described above is the same. Basically the only difference between methods is the use or non-use of the forked cannula 40.

It is understood that the above-described embodiment is merely illustrative of the application. Other embodiments may be readily devised by those skilled in the art which will embody the principles of the invention and fall within the spirit and scope of the invention thereof.

I claim:

1. A method for harvesting bone through a guided delivery instrumentation system which operates through a percutaneous, laparoscopic, minimally-invasive technique, comprising the steps of:

making a small incision above a harvest site;

inserting an elongated guide wire with a blunt proximal end and a pointed distal end into the incision, distal end first, to a bone area to be harvested;

gently impacting the guide wire proximal end whereby the guide wire distal end enters into said bone area in the harvest site;

placing a cylindrical obturator with a generally cylindrical channel centrally formed within said obturator along its central longitudinal axis concentrically over the guide wire;

guiding the obturator onto to the guide wire toward the guide wire distal end whereby the obturator gradually splits muscle and tissue until it contacts said bone;

placing a first, hollow, cylindrical dilator concentrically over said obturator thereby increasing said incision to a percutaneous approach;

removing said guide wire and obturator;

placing an impactor cap over said first dilator;

gently tapping said first dilator with *said* impactor cap into said harvest site bone;

inserting an elongated, hollow, cutting cylinder, said cutting cylinder having a handle on a proximal end and a hollow and a cutting tip on a distal end, into said first dilator whereby said cutting tip is brought into engagement with said bone;

cutting a portion of said bone with said cutting tip and bringing said cut portion through the hollow cutting tip into the cutting cylinder;

removing the cutting cylinder and cutter tip from the first dilator;

removing the handle from said cutter cylinder;

removing the cut bone from the cutter cylinder;

removing the first dilator from said harvest site; and closing the incision.

2. A method for harvesting bone as described in claim 1, further comprising the step of:

placing a second, hollow, cylindrical dilator concentrically over said first dilator.

3. A method for harvesting bone as described in claim 2, further comprising the step of:

placing a third, hollow, cylindrical dilator concentrically over said second dilator.

4. A method for harvesting bone as described in claim 1, further comprising the steps of:

placing a hollow, cylindrical cannula having a proximal end and distal end, said distal end being longitudinally notched resulting in two protruding arms parallel to the central axis of said cannula, concentrically over said dilator whereby said cannula distal end engages the bone area;

placing an impactor cap over said cannula; and gently tapping said cannula with [impact] *said impactor* cap into said bone area.

5. A method for harvesting bone as recited in claim 4, further comprising the step of:

placing a second, hollow, cylindrical dilator concentrically over said first dilator.

6. A method for harvesting bone as recited in claim 5, further comprising the step of:

placing a third, hollow, cylindrical dilator concentrically over said second dilator.

7. A method for harvesting bone as recited in claim 4, further comprising the steps of:

removing said dilator prior to insertion of said cutter cylinder; and inserting said cutting cylinder into said cannula.

8. A bone harvesting apparatus for the removal of bone material from a living body, comprising:

a guided delivery system, comprising:

an elongated guide wire having a pointed distal end and a blunt proximal end, said distal end being adapted to engage a bone from which bone material is to be extracted;

a generally cylindrical obturator with an internal, hollow channel formed along an elongated central axis and positioned concentrically over said guide wire, said obturator having a generally dome-shaped distal end adapted to dividing tissue abutting said bone, and a proximal end with gripping means;

a generally cylindrical, hollow, open-ended dilator concentrically positioned over said obturator; and a generally cylindrical, hollow, open-ended, forked cannula concentrically positioned over said dilator; and a coring device within said delivery system for extracting precise amounts of bone material.

9. A bone harvesting apparatus as recited in claim 8, wherein said guided delivery system is further comprised of:

a plurality of generally cylindrical, hollow, open-ended dilators concentrically positioned over said obturator.

10. A bone harvesting apparatus as recited in claim 8, wherein:

said dilator has a proximal end and a beveled distal end with teeth protruding therefrom.

11. A bone harvesting apparatus as recited in claim 10, wherein said coring device is comprised of:

a cutter cylinder having a proximal end and a distal end interconnected by a hollow tube;

a hollow cutting tip attached to said cutter cylinder distal end;

a handle joined to said cutter cylinder proximal end;

wherein said cutter cylinder and cutting tip are adapted to fitting within said dilator.

12. A bone harvesting apparatus as recited in claim 10, wherein:

said forked cannula has a proximal end terminating in two parallel, block-like elements, and a distal end longitudinally notched resulting in two longitudinally protruding arms parallel to a central, longitudinal cannula axis.

13. A bone harvesting apparatus as recited in claim 12, wherein said coring device is comprised of:

a cutter cylinder having a proximal end and a distal end interconnected by a hollow tube;

a hollow cutting tip attached to said cutter cylinder distal end;

a handle joined to said cutter cylinder proximal end;

wherein said cutter cylinder and cutting tip are adapted to fitting within said dilator.

14. A bone harvesting apparatus as recited in claim 11, wherein:

said cutting tip has a proximal end joined to the cutter cylinder distal end and a distal end having two, protruding, generally triangular flat blades, each having two lateral sides and a distal tip, said distal tips being connected to each other, each said blade lateral side being formed into a cutting edge, said cutting tip distal end also terminating in two cutting edges positioned between said protruding blades.

15. A bone harvesting apparatus as recited in claim 13, wherein:

said cutting tip has a proximal end joined to the cutter cylinder distal end and a distal end having two, protruding, generally triangular flat blades, each having two lateral sides and a distal tip, said distal tips being connected to each other, each said blade lateral side being formed into a cutting edge, said cutting tip distal end also terminating in two cutting edges positioned between said protruding blades.

*16. A method of harvesting bone, the method comprising:*

*inserting a guidance member through a percutaneous incision to a bone, at a bone harvest site;*

*sequentially inserting at least one member of a set of dilation channels through the incision with a first dilation channel of the set having been positioned over the guidance member;*

*inserting a cutter device through the member of the set of dilation channels to engage the bone harvest site; and*

*cutting the bone with the cutter device to bring a portion of the bone into the cutter device's interior.*

*17. A method according to claim 16, the method further comprising:*

*making a percutaneous incision, that is at most 2 centimeters in length, above the bone harvest site.*

*18. A method of harvesting bone, the method comprising:*

*creating a conduit from a patient's skin to a bone harvest site through a small incision in the patient's skin;*

*expanding the diameter of the conduit by inserting, into the small incision, a dilation channel;*

*inserting a cutter device, comprising a hollow collection shaft, into the small incision; and*

*expanding the diameter of the conduit by inserting a plurality of dilation channels of sequentially increasing size.*

* * * * *